(12) United States Patent
Kyyrö et al.

(10) Patent No.: US 11,914,842 B1
(45) Date of Patent: Feb. 27, 2024

(54) DYNAMIC APPLICATION ICONS

(71) Applicant: Oura Health Oy, Oulu (FI)

(72) Inventors: Mats Mikael Kyyrö, Oulu (FI); Antti Oskari Laitala, Oulu (FI); Matias Kukka, Oulu (FI); Ralph Morales, Saratoga, CA (US)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/324,570

(22) Filed: May 26, 2023

(51) Int. Cl.
*G06F 3/04817* (2022.01)
*G06F 3/0482* (2013.01)

(52) U.S. Cl.
CPC ........ *G06F 3/04817* (2013.01); *G06F 3/0482* (2013.01)

(58) Field of Classification Search
CPC .................... G06F 3/04817; G06F 3/0482
See application file for complete search history.

(56) References Cited

U.S. PATENT DOCUMENTS

| | | | |
|---|---|---|---|
| 7,603,629 B1* | 10/2009 | Crosswhite | G06F 3/04817 715/772 |
| 10,606,443 B2* | 3/2020 | Rolih | G06Q 30/0277 |
| 2015/0350414 A1* | 12/2015 | Park | G06F 3/04817 455/566 |
| 2016/0360336 A1* | 12/2016 | Gross | H04W 4/025 |
| 2019/0138186 A1* | 5/2019 | Rolih | H04L 67/55 |

* cited by examiner

*Primary Examiner* — Mong-Shune Chung
(74) *Attorney, Agent, or Firm* — Holland & Hart LLP

(57) ABSTRACT

Methods, systems, and devices for dynamic application icons are described. The application may receive, as part of an application downloading operation, an application software package. The application software package may include a plurality of icons that are configured to visually distinguish the application on a user interface of the user device from other applications running on an operating system of the user device. The application may identify a satisfaction of an achievement threshold corresponding to an alternate icon based on processing data. The application may output, to the operating system of the user device, a visual display instruction to display the alternate icon on the user interface instead of the default icon based on identifying the satisfaction of the achievement threshold. The alternate icon may be visually representative of a type of achievement corresponding to the achievement threshold.

20 Claims, 9 Drawing Sheets

DYNAMIC APPLICATION ICONS

FIELD OF TECHNOLOGY

The following relates to wearable devices and data processing, including dynamic application icons.

BACKGROUND

A user device may display icons on a home screen that identifies applications that are installed on the user device. An application's default icon may be the same for every user of that application and is static, regardless of how the application is used or what data the user enters into the application.

In some cases, health insights may be provided to the user via the application (e.g., a mobile application) that is configured to receive data from the wearable device. In some cases, the application may issue "in-app" rewards to indicate that the user has achieved some accomplishment within the application. But existing applications may not allow for the in-app achievements to be visually recognized outside of the application.

DETAILED DESCRIPTION

Figure 1:
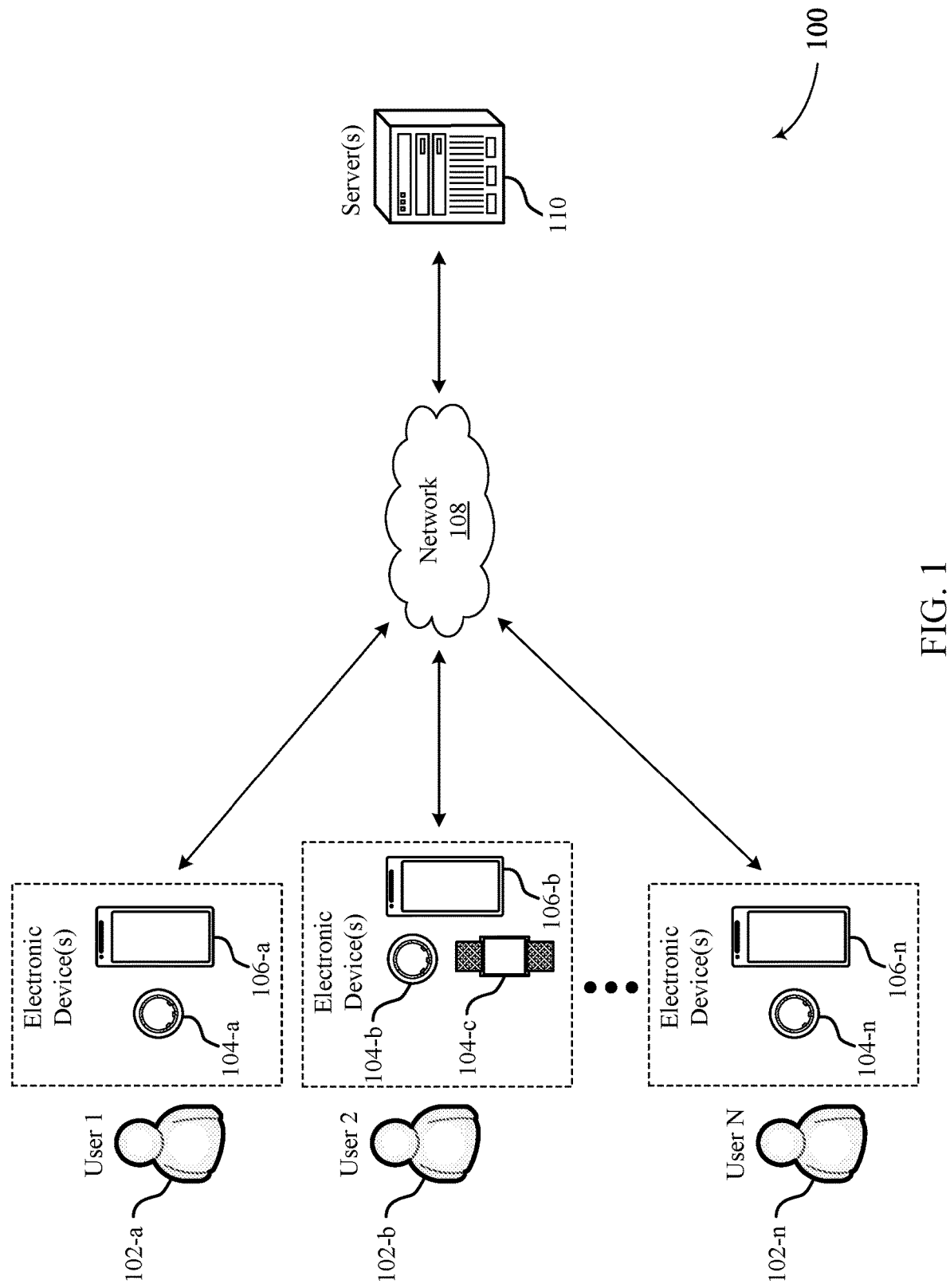
FIG. 1 illustrates an example of a system that supports dynamic application icons in accordance with aspects of the present disclosure.

Some user devices (e.g., a mobile phone or tablet) may display icons on a home screen that identifies applications that are installed on the user device. Typically, an application's icon (i.e., the "default icon") is the same for every user of that application and is static, regardless of how the application is used or what data the user enters into the application. Some applications may issue "in-app" badges, icons, or rewards to indicate that the user has achieved some accomplishment within the application. But existing applications may not allow for such in-app achievements to be visually recognized external to the application (e.g., on the home screen of the user interface or via the icon itself). Rather, the application may display measured physiological data, achievements, patterns, in-app badges, messaging, and the like to the user via a user interface in the application. In such cases, in-app achievements may be visually recognized internal to the application.

However, the application's icon, such as the content displayed to the user external to the application and/or on the home screen of the user interface, may be consistent across users, even if different users have wide variations in their personal goals and achievements. In such cases, applications associated with wearable devices may lack the functionality to personalize the application icon displayed for a particular user. As such, conventional techniques for improved application icon customization are desired.

Aspects of the present disclosure are directed to techniques for application icon personalization. For example, the system may swap out the default application icon on the home screen with an alternative application icon based on the user reaching some achievement within the application. The alternative application icons may be downloaded with the application onto the user device, but may be locked or otherwise invisible to the user until a corresponding achievement is reached. For example, the alternative application icons may be unlocked for use (e.g., display) after some data within the application satisfies a threshold and a reward is achieved. In some examples, the system may receive physiological data from a wearable device associated with the user and identify that the physiological data satisfies the threshold. In such cases, the system may identify that the achievement is reached based on the physiological data received and the threshold being satisfied.

The application may communicate with the operating system of the user device to change the default application icon to an alternative application icon that represents the reward that is achieved. For example, the application may output, to the operating system, an instruction to display the alternative application icon on the home screen of the user device instead of the default application icon. In such cases, the default application icon may be switched to the alternative application icon. The alternative application icon may represent a type of achievement (e.g., an activity-based achievement, a sleep-based achievement, a Readiness-based achievement, a recovery-based achievement, or any combination thereof). In some cases, the type of achievement may be a money-based achievement, an enrollment in a subscription service, and the like.

The system may allow for customization and personalization of the application icons on the home screen of the user device based on data received at the application and achievements within the application. In such cases, the system may increase the value of the accomplishments within the application by making the application icon on the home screen more personal, engaging, and representative of the accomplishment. The system may optimize the user experience such that the "in-app" badges, icons, or rewards that indicate that the user has achieved an accomplishment within the application is visually displayed outside of the application and on the home screen of the user device.

Aspects of the disclosure are initially described in the context of systems supporting physiological data collection from users via wearable devices. Aspects are then described in the context of graphical user interfaces and process flow diagrams. Aspects of the disclosure are further illustrated by and described with reference to apparatus diagrams, system diagrams, and flowcharts that relate to dynamic application icons.

FIG. 1 illustrates an example of a system 100 that supports dynamic application icons in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5)

multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for a system 100 that changes the default application icon on the home screen of the user device 106 to an updated application icon based on an achievement being reached by the user 102. The achievement being reached may be based on at least some data received from a wearable device 104, data received from other sources (e.g., other applications), or both. For example, the system 100 may receive, as part of an application downloading operation to the user device 106, an application software package for an application that is configured for processing data received from the wearable device 104, from other sources (e.g., other applications), or both. The application may run on an operating system of the user device 106. In some cases, the application software package may include a plurality of icons that are configured to visually distinguish the application on a user interface of the user device 106 from other applications running on the operating system of the user device 106. The plurality of icons may include at least a default icon and one or more alternate icons that correspond to one or more achievement thresholds.

The system 100 may identify a satisfaction of a first achievement threshold of the one or more achievement thresholds corresponding to a first alternate icon of the one or more alternate icons in response to processing data received at the application. The system 100 may output, to the operating system of the user device 106, a visual display instruction to display the first alternate icon on the user interface of the user device 106 instead of the default icon based on identifying the satisfaction of the first achievement threshold. The visual display instruction may include an instruction for switching the default icon to the first alternate icon where the first alternate icon may visually represent of a type of achievement corresponding to the first achievement threshold.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
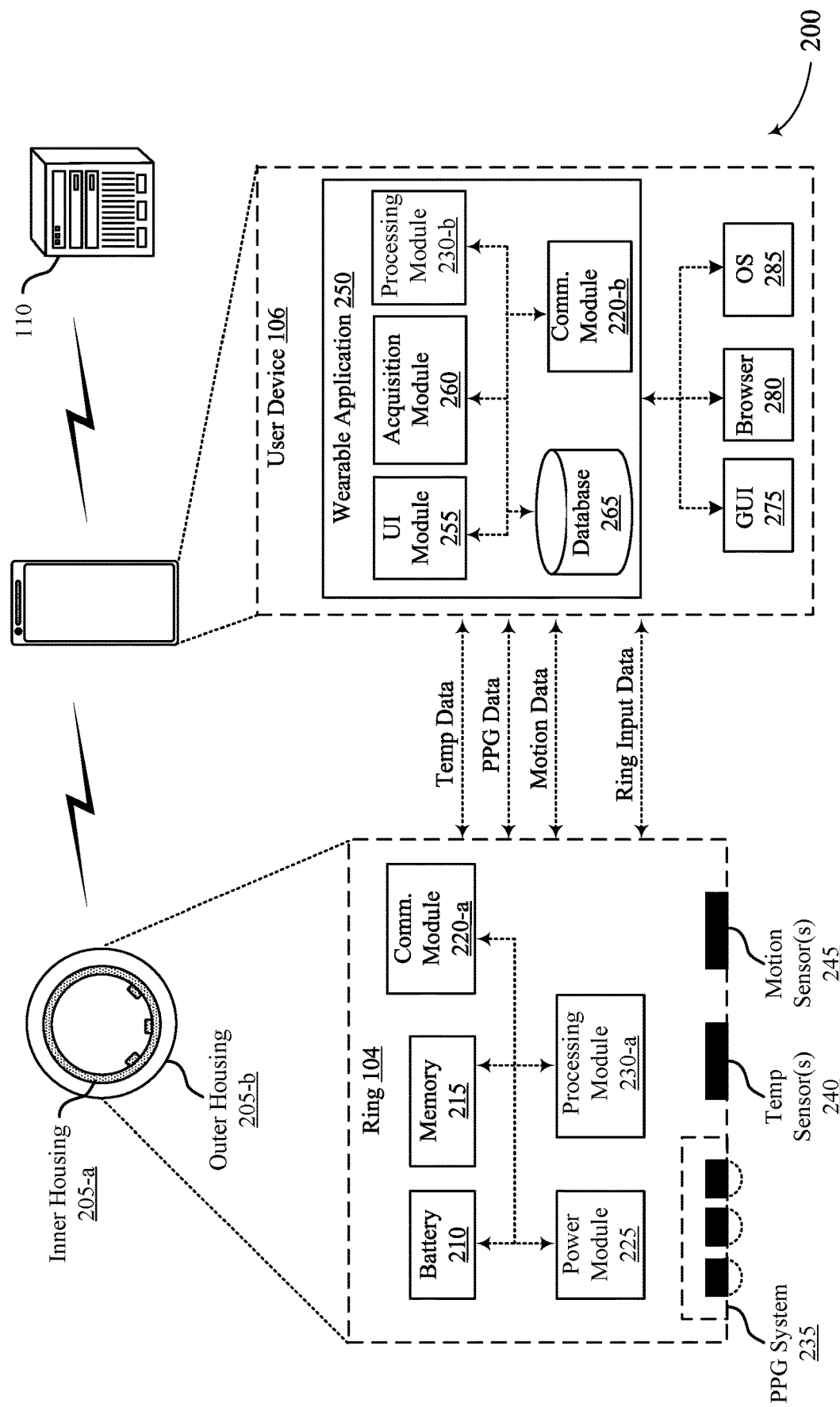
FIG. 2 illustrates an example of a system that supports dynamic application icons in accordance with aspects of the present disclosure.

FIG. 2 illustrates an example of a system 200 that supports dynamic application icons in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, that may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/ different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/ external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for dynamic application icons that allow for customization and personalization of the application icons on the home screen or other user interface of the user device 106 based on data received at the application and achievements within the application. For example, as described previously, the system 200 (e.g., including the wearable application 250) may process data received at the wearable application 250 from at least the wearable device 104. In such cases, the system 200 may receive, at the application, physiological data measured from a user by the wearable device 104. In some examples, the data received at the application from which the achievements are determined may be received from sources other than, or in addition to, a wearable device 104. For example, data may be generated within the application, based on user input, pulled from other applications running on the user device 106, among other examples.

For example, as noted previously herein, the ring 104 of the system 200 may be worn by a user to collect data from the user, including temperature data, sleep data, recovery data, activity data, heart rate data, HRV data, respiratory data, breathing rate data, blood pressure data, blood glucose data, stress level, and the like. The ring 104 of the system 200 may collect the physiological data from the user based on temperature sensors and measurements extracted from arterial blood flow (e.g., using PPG signals). In some cases, the ring 104 may collect the physiological data from the user based on measurements extracted from capillary blood flow, arteriole blood flow, or both. The physiological data may be collected continuously.

In some implementations, the processing module 230-*a* may sample the user's temperature continuously throughout the day and night. Sampling at a sufficient rate (e.g., one sample per minute) throughout the day and/or night may provide sufficient temperature data for analysis described herein. In some implementations, the ring 104 may continuously acquire temperature data (e.g., at a sampling rate). In some examples, even though temperature is collected continuously, the system 200 may leverage other information about the user that it has collected or otherwise derived (e.g., sleep stage, activity levels, illness onset, etc.) to select a representative temperature for a particular day that is an accurate representation of the underlying physiological phenomenon.

The system 200 may identify a satisfaction of an achievement threshold corresponding to an alternate icon based on processing the data (e.g., including at least the physiological data or other types of data). For example, the system 200 may identify that the user has completed some achievement or goal related to sleep, activity, mindfulness, nutrition, or any other category, by measuring or processing data received at the wearable application 250. In other examples, the system 200 may identify that the user has completed some achievement or goal related to a threshold amount of money in their savings account, a quantity of followers on a social media account, or any other category. In some cases, the system 200 may receive an application software package for the application as part of an application downloading operation to the user device 106. In such cases, the application may run on an operating system 285 of the user device 106, and the application software package may include icons that are configured to visually distinguish the application on a user interface (e.g., GUI 275) of the user device 106 from other applications running on the operating system 285 of the user device 106.

The icons may include at least a default icon and alternate icons that correspond to achievement thresholds. A default icon may refer to the icon that typically is associated with the application as determined by the application developer (e.g., when initially downloaded from an application marketplace or platform). The wearable application 250 may transmit, to the operating system 285 of the user device 106, a visual display instruction to display the alternate icon on the user interface (e.g., GUI 275) of the user device 106 instead of the default icon after identifying the satisfaction of the achievement threshold. The alternate icon may be visually representative of a type of achievement corresponding to the achievement threshold.

Figure 3:
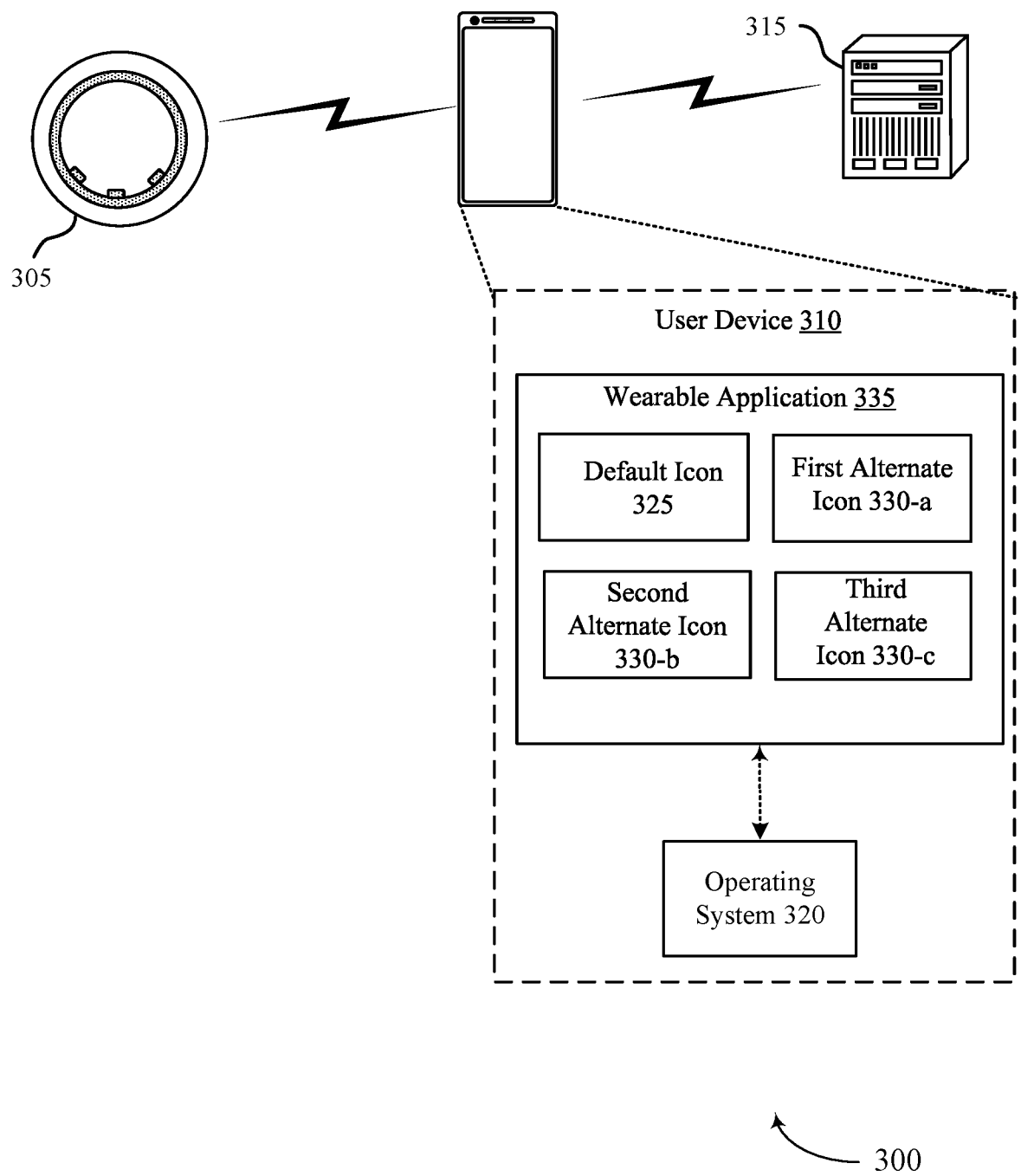
FIG. 3 shows an example of a system that supports dynamic application icons in accordance with aspects of the present disclosure.

FIG. 3 shows an example of a system 300 that supports dynamic application icons in accordance with aspects of the present disclosure. The system 300 may implement, or be implemented by, system 100, system 200, or both. In particular, system 300 illustrates an example of a wearable device 305 (e.g., ring 104), a user device 310 (e.g., user device 106), and a server 315 (e.g., server 110), as described with reference to FIGS. 1 and 2.

A user may use a wearable device 305, for example, a ring to collect, monitor, and track physiological data of the user based on measurements collected via one or more sensors of the wearable device 305, as described with reference to FIG. 2. In some cases, the wearable device 305 may be an example of a finger-worn device, a wrist-worn device, a patch, a head-worn device, a chest-worn device, or a combination thereof. The wearable device 305 may be configured to collect, store, and/or process data (e.g., including physiological data), and may transfer any of the data described herein to the user device 310 for storage and/or processing.

The user device 310 may include an operating system 320 (e.g., operating system 285) and a wearable application 335 (e.g., wearable application 250). The wearable application 335 may be an example of an application (e.g., "app") that may be installed on the user device 310 and configured to acquire data from the wearable device 305, store the acquired data, and process the acquired data as described herein. For example, the wearable application 335 may receive physiological data measured from a user by the wearable device.

The wearable application 335 may receive an application software package as part of a downloading operation (e.g., from an application marketplace, application store, or the like). For example, the wearable application 335 may receive the application software package as a part of an update to the wearable application 335 that has already been previously downloaded to the user device 310 or an initial download of the wearable application 335 to the user device 310.

The wearable application 335 may run on the operating system 320 of the user device 310. The wearable application 335 may include at least default icon 325, and one or more alternate icons (e.g., a first alternate icon 330-*a*, a second alternate icon 330-*b*, and a third alternate icon 330-*c*). For example, the application software package may include a list of icons (e.g., including the default icon 325, the first alternate icon 330-*a*, the second alternate icon 330-*b*, and the third alternate icon 330-*c*) that each visually distinguish the wearable application 335 on a user interface of the user device 310 from other applications running on the operating system 320. In such cases, the wearable application 335 may receive the list of icons as part of the application downloading operation, thereby downloading the list of icons with the wearable application 335 onto the user device 310.

The default icon 325 may identify the wearable application 335 that is installed on the user device 310, and the alternate icons 330 may each identify an achievement received within the wearable application 335 that is installed on the user device 310. The default icon 325 may be displayed, via the user interface of the user device 310, to the user and the alternate icons (e.g., including the first alternate icon 330-a, the second alternate icon 330-b, and the third alternate icon 330-c) may be invisible to the user or otherwise locked from use and display until an accomplishment is achieved. For example, the first alternate icon 330-a, the second alternate icon 330-b, and the third alternate icon 330-c may be stored in the user device 310 and unable to be displayed until a threshold is achieved for the accomplishment. In such cases, each alternate icon may include a corresponding achievement threshold such that when the threshold is satisfied, the user achieves the accomplishment, and the alternate icon is unlocked and able to be displayed.

For example, the first alternate icon 330-a may be associated with an activity-based achievement and include an achievement threshold such as a value corresponding to the activity-based achievement. For example, the achievement threshold may be an example of a quantity of minutes that the user exercises per day/per week/per month, a frequency at which the user exercises per week, an average mile pace, a quantity of marathons completed by the user, and the like. The wearable application 335 may receive activity data from the wearable device 305 (and/or other sources), and the wearable application 335 may compare the activity data received to the achievement threshold (e.g., the value corresponding to the activity-based achievement).

The wearable application 335 may identify whether the activity-based achievement is reached. The activity-based achievement may be an example of completing one hour of active minutes a day, exercising five days per week, running a 6 minute mile pace or less, completing a marathon, and the like. The wearable application 335 may identify a satisfaction of a first achievement threshold (e.g., the activity-based achievement threshold) corresponding to the first alternate icon 330-a of the one or more alternate icons in response to processing data received at the wearable application 335 from at least the wearable device 305. For example, the wearable application 335 may receive data indicating the user completed a marathon, and identify the satisfaction of the first achievement threshold. The wearable application 335 may unlock the first alternate icon 330-a for use to be displayed on the home screen of the user device 310 in response to identifying the satisfaction of the first achievement threshold.

The second alternate icon 330-b may be associated with a sleep-based achievement. The second alternate icon 330-b may include an achievement threshold such as a value corresponding to the sleep-based achievement. For example, the sleep-based achievement may be an example of a duration of time that the user sleeps per night, a quantity of minutes that the user spends in deep sleep per night, a time that the user goes to bed each night, a time that the user wakes up each morning, and the like. The wearable application 335 may receive sleep data from the wearable device 305 (and/or other sources) where the sleep data may include a duration of time that the user sleeps per night, a quantity of minutes that the user spends in deep sleep per night, a time that the user goes to bed each night, a time that the user wakes up each morning, and the like.

The wearable application 335 may compare the sleep data received to the achievement threshold (e.g., the value corresponding to the sleep-based achievement), and identify whether the sleep-based achievement is reached. For example, the sleep-based achievement threshold may be sleeping at least eight hours each night for seven consecutive days. The received sleep data may indicate the user slept at least eight hours each night for seven consecutive days, and the wearable application 335 may identify a satisfaction of a second achievement threshold (e.g., the sleep-based achievement threshold) corresponding to the second alternate icon 330-b of the one or more alternate icons. The wearable application 335 may unlock the second alternate icon 330-b for use to be displayed on the home screen of the user device 310 in response to identifying the satisfaction of the second achievement threshold. In other examples, the received sleep data may indicate the user slept at least eight hours each night for five consecutive days, and the wearable application 335 may not identify a satisfaction of the second achievement threshold and refrain from unlocking the second alternate icon 330-b for use.

The third alternate icon 330-c may be associated with a recovery-based achievement, and the third alternate icon 330-c may include an achievement threshold such as a value corresponding to the recovery-based achievement. The recovery-based threshold may be an example of a quantity of times that the user completes a meditation per week, a duration of time that the user rests per day/per week, a duration of time between activities, and the like. The wearable application 335 may receive the recovery data and determine whether the received recovery data satisfies the achievement threshold (e.g., the recovery-based achievement threshold).

The wearable application 335 may determine that the received recovery data satisfies (e.g., exceeds the threshold), and identify that the recovery-based achievement is met. For example, the recovery-based achievement threshold may be an example of completing a meditation every day for a week. The received data may indicate the user completed a meditation for seven consecutive days, and the wearable application 335 may identify a satisfaction of a third achievement threshold (e.g., the recovery-based achievement threshold) corresponding to the third alternate icon 330-c. In such cases the third alternate icon 330-c may be unlocked for use and visible to the user for selection and display on the home screen of the user device 310. In other examples, the received recovery data may indicate the user completed a single mediation the past week, and the wearable application 335 may not identify a satisfaction of the third achievement threshold and refrain from unlocking the third alternate icon 330-c for use.

In such cases, the user may achieve the accomplishment within the wearable application 335, and the wearable application 335 may unlock one or more alternate icons 330 and allow the user the ability to select which alternate icon 330 to display on the home screen. In response to identifying the satisfaction of the achievement threshold, the wearable application 335 may communicate with the operating system 320 of the user device 310 to change the default icon 325 to one of the alternate icons 330 that represents the accomplishment. For example, the wearable application 335 may output, to the operating system 320, an instruction to display the first alternate icon 330-a, the second alternate icon 330-b, or the third alternate icon 330-c on the home screen of the user device 310 instead of the default icon 325. In such cases, the default icon 325 may be switched to the first alternate icon 330-a, the second alternate icon 330-b, or the third alternate icon 330-c.

In some cases, if more than one alternate icon 330 is unlocked for use (e.g., the achievement threshold is satisfied for more than one achievement), the user may select which alternate icon 330 may be displayed on the user device 310. For example, the wearable application 335 may output a request to select the first alternate icon 330-a or the second alternate icon 330-b in response to identifying the satisfaction of the first achievement threshold and the second achievement threshold. In other examples, the wearable application 335 may output a request to select the first alternate icon 330-a, the second alternate icon 330-b, or the third alternate icon 330-c in response to identifying the satisfaction of each achievement threshold (e.g., the first achievement threshold, the second achievement threshold, and the third achievement threshold).

The wearable application 335 may receive a selection of one of the alternate icons 330. For example, the wearable application 335 may receive a selection of the second alternate icon 330-b, and the wearable application 335 may output, to the operating system 320 of the user device 310, a second visual display instruction to display the second alternate icon 330-b instead of the default icon 325, or if previously unlocked and/or displayed, the first alternate icon 330-a. In other examples, the wearable application 335 may receive a selection of the third alternate icon 330-c, and the wearable application 335 may output, to the operating system 320, a third visual display instruction to display the third alternate icon 330-c instead of the default icon 325, or if previously unlocked and/or displayed, the first alternate icon 330-a or the second alternate icon 330-b.

After more than one alternate icon 330 is unlocked and able to be selected (e.g., displayed), the user device 310 may include a list of available alternate icons 330 where the user may select between multiple alternate icons 330 that have been previously unlocked. In such cases, the achievements may be unlocked as alternate icons 330 that allow for customization and personalization of the home screen on the user device 310. The alternate icons 330 may be seen as a badge of honor that may be displayed and shared via the home screen on the user device 310 rather than having to access the wearable application 335 to view the achievements. The data within the wearable application 335 may be viewed outside of the wearable application 335, allowing for increased personalization of the home screen based on achievements reached within the wearable application 335.

In some cases, the alternate icons 330 may motivate or encourage the users to achieve goals related to sleep, activity, recovery, Readiness, and the like. For example, by using the physiological data detected via the wearable device 305, the user interface of the user device 310 may be altered to display the alternate icons 330 associated with the goal achieved. The alternate icons 330 may be awarded to the user as rewards based on detected physical activities of the user, sleep accomplishments, and the like. In such cases, the user interface of the user device 310 may be more engaging and rewarding to the user.

In some examples, the wearable application 335 may generate a cryptocurrency-based reward for the user based on identifying the satisfaction of the first achievement threshold. The cryptocurrency-based reward may represent an award and/or achievement received within the wearable application 335. In some cases, the cryptocurrency-based reward may visually represent a type of cryptocurrency token that has been received within the wearable application 335 based on an achievement by the user.

The wearable application 335 may award the user with one or more cryptocurrency rewards (e.g., tokens) once they achieve their goals. In some cases, an amount of cryptocurrency rewarded may depend on the difficulty of the goal, the level of achievement, a frequency of achieving the goal, or a combination thereof. For example, after the wearable application 335 recognizes that the user has achieved a status and/or goal (e.g., identifies a satisfaction of a first achievement threshold), the cryptocurrency-based reward is generated. The tokens may be an example of a cryptocurrency token, a non-fungible token, a smart contract enabled token, or a combination thereof.

In some examples, a cryptocurrency-based reward (e.g., including one or more tokens) may leverage a decentralized network and/or smart contract to simplify the gamification of sleep measured via the wearable application 335. For example, the wearable application 335 may administer sleep tokens associated with a type of cryptocurrency to reward users for achieving a sleep goal, a sleep target, a Sleep score, or a combination thereof. In such cases, the cryptocurrency-based reward generated and insights displayed to the user by the wearable application 335 may be gamified to encourage positive health benefits. In some cases, the cryptocurrency-based reward may be an example of an ERC-2o token that may reward the user for healthy habits (e.g., achieving a sleep goal, activity goal, a Readiness score, and the like). The ERC-20 tokens may be an example of a type of cryptocurrency that are built on top of the Ethereum blockchain. The ERC-20 tokens may be used to represent assets like shares, loyalty points, or even other cryptocurrencies and may be traded on cryptocurrency exchanges like other cryptocurrencies.

In some cases, the wearable application 335 may include a blockchain address. For example, the user may link a cryptocurrency wallet to the wearable application 335, and the wearable application 335 may track the user's progress towards the achievement (e.g., goal). The wearable application 335 may transmit instructions to a blockchain platform to generate the cryptocurrency-based reward in response to achieving the goal. In such cases, the wearable application 335 may initiate a transaction to record the generation of the token (e.g., the cryptocurrency-based reward) on a blockchain platform (e.g., Ethereum, IBM Blockchain, Hyperledger Fabric, and the like). The achievements awarded within the wearable application 335 may be supported by a blockchain transaction.

In some cases, the system 300 may connect a membership associated with the wearable application 335 to a cryptocurrency wallet or may serve as a cryptocurrency exchange. A cryptocurrency wallet may be an example of a software program or a hardware device that stores public and private keys used to send and receive digital currency. The system 300 may include near-field communication (NFC) to enable exchanging cryptocurrency (e.g., cryptocurrency-based rewards) obtained from achieving goals within the wearable application 335. In some cases, the cryptocurrency-based reward may be an example of a cryptocurrency token that may be used for purchases within the wearable application 335 or outside the wearable application 335 (e.g., within other applications on the user device 310). For example, the cryptocurrency token may be an example of Bitcoin.

To keep the user motivated and engaged, the wearable 335 application may offer challenges and competitions with other users, where the users may earn additional rewards (e.g., a cryptocurrency-based rewards) for completing specific challenges or achieving certain milestones. The wearable 335 application may provide users with a unique incentive to achieve their goals and earn cryptocurrency rewards, while also promoting healthy lifestyles and physical activity.

Figure 4:
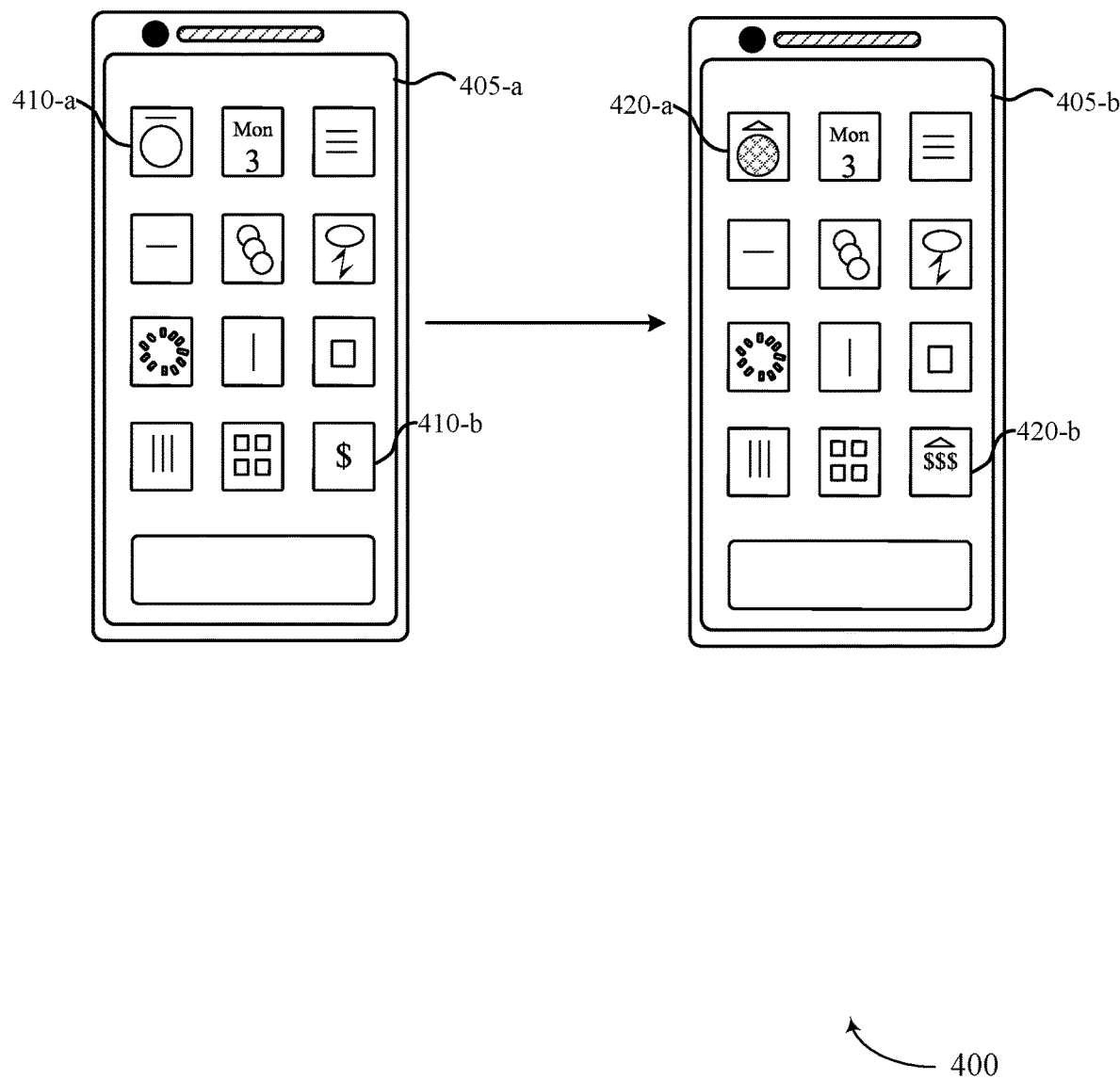
FIG. 4 shows an example of a user device that supports dynamic application icons in accordance with aspects of the present disclosure.

FIG. 4 shows an example of a user device 400 that supports dynamic application icons in accordance with aspects of the present disclosure. The user device 400 may implement, or be implemented by, aspects of the system 100, system 200, system 300, or any combination thereof. For example, the user device 400 may be an example of a user device 106 (e.g., user device 106-a, 106-b, 106-c) corresponding to a user. The user device 400 may include a GUI 405 that may be an example of a GUI 275 of a user device 106 (e.g., user device 106-a, 106-b, 106-c).

In some examples, the GUI 405 displays a home screen of the user device 400. The operating system of the user device 400 may cause the GUI 405 to display a plurality of application icons (e.g., icons 410, 420). The application icons may be configured to identify a type of application that is installed on the user device 400 or otherwise visually distinguish applications from each other.

The GUI 405-a may include a plurality of default icons 410 that may identify the corresponding application that are installed on the user device 400. For example, the first default icon 410-a may be associated with a wearable application, as described with reference to FIGS. 2 and 3. A second default icon 410-b may be associated with a different application such as a money management application. The application's icon (e.g., the first default icon 410-a and the second default icon 410-b) may be consistent across users. That is, all users that download a particular application may see the same default icon. In such cases, the content displayed to the user external to the application and/or on the home screen of the GUI 405 via the first default icon 410-a and the second default icon 410-b may be the same for different users regardless of the information within the application. Some applications may issue a badge, icon, or reward within the application to indicate that the user has achieved some accomplishment within the application. However existing applications may not allow for the accomplishments achieved within the application to be displayed on the home screen of the GUI 405 or via the default application icon 410 on the home screen (e.g., external to the application).

As described herein, the alternate icons 420 may each identify an achievement received within the wearable application that is installed on the user device 400. After a visual display instruction is outputted to the operating system of the user device 400, the default icons 410 may be swapped out for the alternate icons 420.

For example, the GUI 405-b of the user device 400 may display the first alternate icon 420-a instead of the first default icon 410-a and display the second alternate icon 420-b instead of the second default icon 410-b. The alternate icons 420 may include different colors, graphics, shapes, sizes, content, messages, or a combination thereof as compared to the default icons 410. Therefore, a first user that has not yet accomplished an achievement within an application or otherwise unlocked an alternate icon may see the default icon 410 for that application, whereas a second user having the same application may see an alternate icon 420 on their device upon accomplishment of an achievement defined within the application.

As described with reference to FIG. 3, the first alternate icon 420-a may visually represent a type of achievement corresponding to an achievement threshold. For example, the type of achievement may be related to the user's sleep, activity, recovery, Readiness, or a combination thereof. The achievement threshold may be an example of a value corresponding to a sleep metric, an activity metric, a recovery metric, a Readiness metric, or a combination thereof.

For example, the first alternate icon 420-a may visually represent that the user is awarded for taking a moment during the day to complete a meditation practice (e.g., a "taking time" award), that the user uses tags and notes within the application (e.g., a "biohacker" award), or that the user completed a nap and increased restorative moments (e.g., a "daydreamer" award). Examples of other awards that may be visually represented via the alternate icon 420-a may include a "over 9,000 steps" award, a "healing" award for increasing a recovery score, a "sporty" award for achieving an activity goal, a "sleeping beauty" award for achieving a sleep goal, and the like. In such cases, the awards achieved within the application may be visually present external to the application by updating the default icon 410-a to the first alternate icon 420-a.

In some cases, the alternate icon 420 may share information with the user without having to open (e.g., access) the application. For example, the first alternate icon 420-a may display a particular color, graphic, shape, or size to indicate whether the user's Readiness Score is low or high, whether the user's Sleep Score is low or high, and the like. In such cases, the first alternate icon 420-a may be a red color if the user's scores are low or a green color if the user's scores are high.

The user may be unaware when they have satisfied a threshold to achieve the goal, thereby unlocking the alternate icon 420 for use and display. In such cases, the user may select the available alternate icon 420 and allow the invisible achievement unknown to the user initially to be a visible achievement outside of the application (e.g., displayed via the alternate icon 420). Rather than sending the achievement via a social share function, the user may personalize the home screen of the user device 400 to display the achievements via the alternate icons 420.

Although updating the default icon 410 may be based at least partially on data received from a wearable device, in some examples, the default icons 410 may be changed based on receiving data from sources other than the wearable device. In such cases, other data sources (e.g., subscription services, partnerships, payments, etc.) may change the default application icon (e.g., second default icon 410-b) to the second alternate icon 420-b. For example, a user with a threshold amount of money in their investment account may have a different icon for their money management application icon as compared with a different user without the threshold amount of money in their investment account. In other examples, a user enrolling in a subscription service may have a different icon for their subscription service icon as compared to a different user that is not enrolled in the subscription service.

In some cases, the application may receive, as part of the application downloading operation to the user device 400, an application software package for an application that is configured for processing data received from other devices, data sources, databases, the user, or a combination thereof. The application software package may include a list of alternate icons 420 that visually distinguish the application on the user interface and include at least a default icon 410-b and one or more alternate icons 420-b. The application may output, to the operating system of the user device 400, a visual display instruction to display the second alternate icon 420-*b* on the GUI 405-*b* of the user device 400 instead of the second default icon 410-*b* based on data received from other data sources.

For example, the application associated with the default icon 410-*b* may receive an indication that an amount of money in the savings account exceeded the user's goal and identify that a satisfaction of the threshold is achieved. The visual display instruction may instruct the operating system to change the default icon 410-*b* to the second alternate icon 420-*b* to visually represent the savings goal achieved. For example, the second alternate icon 420-*b* may include a change in color, a change in graphic, a change in words, or a combination thereof. In some cases, the user may select the threshold for the application to reflect the user's personal money management goal. For example, the application may receive an indication of the threshold amount of money in the savings account, and the application may set the threshold to indicate the received threshold. In other examples, the application software package may include a default threshold associated with the achievement to unlock the second alternate icon 420-*b*.

In other examples, the default icon 410 may be updated based on a subscription service enrolled in by the user. For example, the user may enroll in a subscription service, and the application may receive an indication of enrollment in the subscription service. The indication of enrollment in the subscription service may be an example of identifying a satisfaction of a threshold. In such cases, the application may identify that satisfaction of the threshold, and the application may output a visual display instruction to display the alternate icon 420-*b* instead of the default icon 410-*b* in response to receiving an indication of enrollment. For example, the application may receive an indication that the user enrolled in a monthly grocery delivery service, and the application may output the visual display instruction to replace the default icon 410 with the alternate icon 420 indicative of the subscription service. In other examples, if the user subscribes to a mailing list associated with the application, the default icon 410 may be switched to display the alternate icon 420.

In some cases, the default icon 410 may be updated based on a partnership, enrollment, or collaboration between the application and the user. For example, the user may enroll in a sleep challenge with a mattress company, and the application may receive an indication of the collaboration, and output a visual display instruction to display the alternate icon 420 instead of the default icon 410 based on the enrollment. In such cases, the indication of the collaboration may be an example of the threshold to satisfy the achievement. The visual display instruction may include instructions to update the default icon 410-*a* associated with the wearable device that receives sleep data, a default icon 410 associated with the company, or both.

In other examples, the user may enroll in an activity challenge with a fitness group. The application may receive an indication of enrollment and output a visual display instruction to display the alternate icon 420 instead of the default icon 410 based on the enrollment. The visual display instruction may include instructions to update the default icon 410-*a* associated with the wearable device that receives activity data, a default icon 410 associated with the fitness group, other default icon associated with the activity, or a combination thereof. In some cases, the default icon 410 may be associated with a social media account, and the default icon 410 may be dynamically updated to the alternate icon 420 after the user achieves a threshold of social media followers, a threshold of social media posts, and the like.

In some cases, the alternate icons 420 may identify a type of hardware associated with the user device 400, a wearable device associated with the application, or both. For example, the system may identify a type of hardware of the wearable device in response to receiving the application software package, and the alternate icon 420 may visually represent the type of hardware. For example, the alternate icon may indicate that the wearable device is a premium or limited edition version of the wearable device. In other examples, the application associated with the default icon 410-*a* may receive data from other applications on the user device 400. In such cases, the application may output display instructions to change the default icon 410 to the alternate icon 420 that is representative of the data received from other applications.

In some examples, the user may purchase an alternate icon 420. For example, the application may receive a payment associated with an alternate icon 420. The application may output, to the operating system, a visual display instruction to display the alternate icon 420 that has been purchased. In such cases, identifying a satisfaction of the threshold may be an example of receipt of payment.

Figure 5:
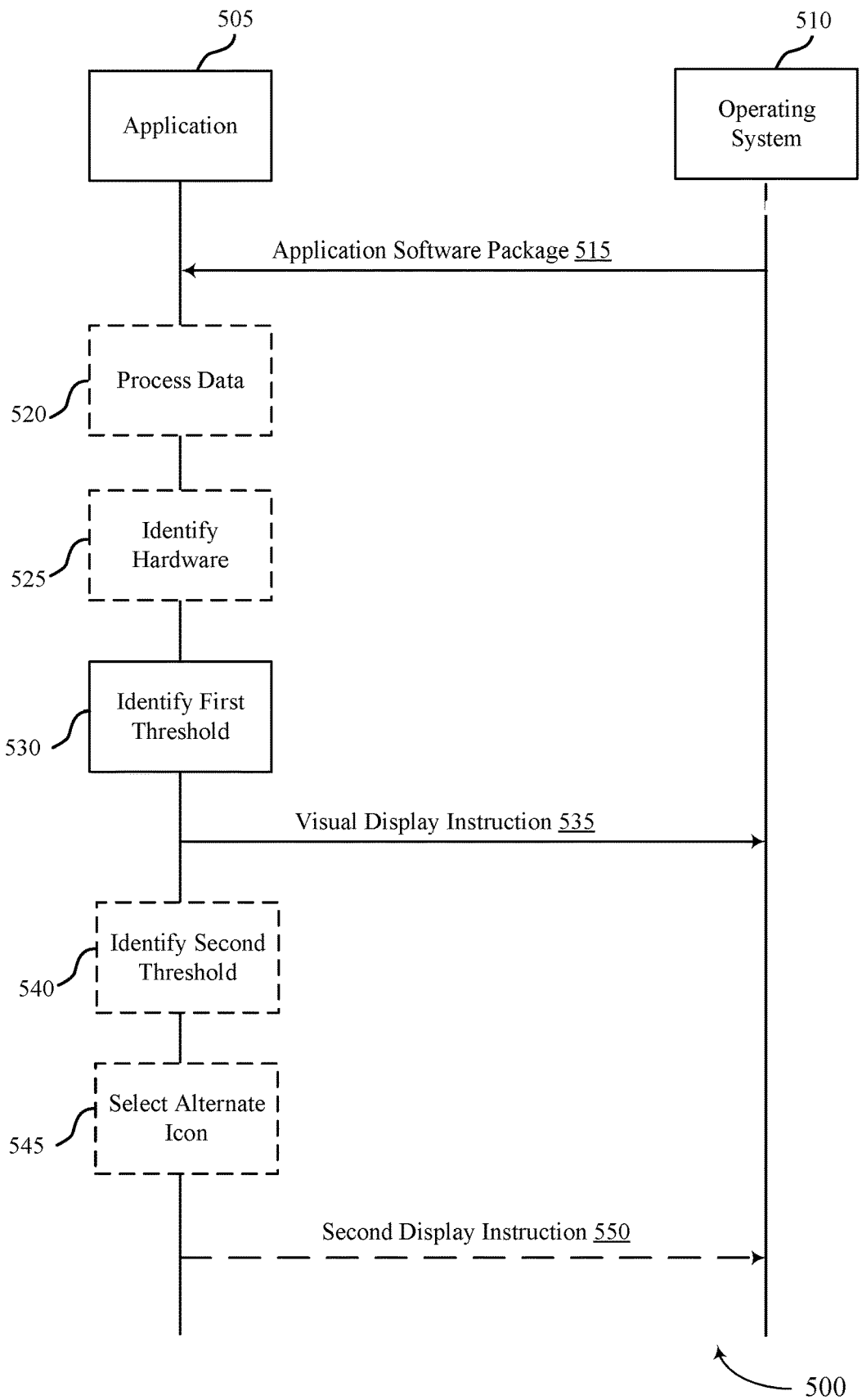
FIG. 5 shows an example of a process flow that supports dynamic application icons in accordance with aspects of the present disclosure.

FIG. 5 shows an example of a process flow 500 that supports dynamic application icons in accordance with aspects of the present disclosure. Process flow 500 may include application 505 and operating system 510, that may be respective examples of an application and operating system as described in reference to FIGS. 1 through 4. In some cases, the application 505 may run on the operating system 510 of the user device.

Alternative examples of the following may be implemented, where some steps are performed in a different order or not at all. Some steps may additionally include additional features not mentioned below. The process flow 500 illustrates techniques where an application 505 outputs visual display instructions to switch a default icon displayed on a user interface of a user device to an alternate icon based on data received at the application 505.

Aspects of the process flow 500 may be implemented by a controller, among other components. Additionally or alternatively, aspects of the process flow 500 may be implemented as instructions stored in memory (e.g., firmware stored in a memory coupled with the application 505, operating system 510, or both). For example, the instructions, if executed by a controller (e.g., the memory system controller), may cause the controller to perform the operations of the process flow 500.

At 515, an application software package may be received. For example, the operating system 510 may transmit the application software package to the application 505. In such cases, the application 505 may receive the application software package as part of an application downloading operation to a user device. In some examples, the application software package may be for an application that is configured for processing data received from a wearable device, as described with reference to FIGS. 2 and 3. The application software package may include icons that are configured to visually distinguish the application 505 on a user interface of the user device from other applications running on the operating system 510 of the user device. For example, the icons may include at least a default icon and one or more alternate icons. In some cases, the alternate icons may be downloaded with application 505 onto the user device, via the application software package, but may be locked for use until a corresponding achievement is reached, as described herein.

At 520, data may be processed. For example, the application 505 may process data received at the application 505 from at least the wearable device. In such cases, the application 505 may receive physiological data measured from a user by the wearable device. The physiological data may include sleep data, recovery data, activity data, heart rate data, breathing rate data, blood pressure data, blood glucose data, or a combination thereof. In other examples, the application 505 may process data received at the application 505 from other data sources including other applications running on the operating system 510, other wearable devices, the user, or a combination thereof. For example, the application 505 may process data received at the application 505 from other sources such as a bank account, a medical account, a social media account, user input, or a combination thereof.

At 525, a hardware may be identified. For example, the application 505 may identify a hardware attribute of the wearable device in response to receiving the application software package. In some cases, the icons may be based on the type of hardware of the wearable device. In such cases, the type of hardware may dictate the appearance of an alternate icon. For example, the alternate icon may be different for a wearable device of a first hardware type as compared to the alternate icon for a wearable device of a second hardware type.

At 530, a first threshold may be identified. For example, the application 505 may identify a first achievement threshold after processing the data. In some cases, the application 505 may identify a satisfaction of a first achievement threshold of the achievement thresholds corresponding to a first alternate icon of the alternate icons. In such cases, the application 505 may identify that the first threshold is satisfied, and the user has achieved some accomplishment within the application 505 in response to receiving the data. In some examples, the application 505 may use physiological data measured by the wearable device to identify that the threshold is met, thereby unlocking the alternate application icon for use and display on the home screen of the user device. In other examples, the application 505 may user data received from other sources such as a bank account, a medical account, a social media account, and/or user input to identify that the threshold is met.

The application 505 may issue an "in-app" badge, icon, or reward to indicate that the user has achieved an accomplishment within the application 505. For example, the application 505 may identify that the user slept more than eight hours each night for the past week, and the alternate icon corresponding to a sleep-based achievement may be unlocked. In such cases, the first threshold may be an example of eight hours slept each night for the past week. In other examples, the application 505 may identify that the user's social media account achieved one million followers, and the alternate icon corresponding to a social media-based achievement may be unlocked. In such cases, the first threshold may be an example of one million followers.

At 535, the visual display instruction may be outputted. For example, the application 505 may generate the visual display instruction and output the visual display instruction to the operating system 510 of the user device. The visual display instruction may include an instruction to display the first alternate icon of the alternate icons on the user interface of the user device instead of the default icon. In some cases, the visual display instruction may be outputted in response to identifying the satisfaction of the first achievement threshold. The application 505 may communicate with the operating system 510 of the user device to change the default application icon to an alternate icon after identifying the first threshold.

For example, the visual display instruction may include an instruction for switching the default icon to the first alternate icon. In such cases, the default icon may be changed and/or updated to the unlocked application icon (e.g., the first alternate icon). The system may swap out the default application icon on the home screen with an alternate, unlocked application icon based on the user reaching some achievement (e.g., the first achievement threshold) within the application 505. The alternate application icon may be visually representative of a type of achievement (e.g., a sleep achievement, an activity achievement, a recovery achievement, a money achievement, and the like) corresponding to the first achievement threshold. For example, the alternate application icon may be visually representative of the sleep-based achievement corresponding to the user sleeping more than eight hours each night. In other examples, the alternate application icon may be visually representative of the social media-based achievement corresponding to the user achieving one million followers on their social media account.

In some cases, the application 505 may generate a cryptocurrency-based reward for the user based on identifying the satisfaction of the first achievement threshold. For example, the cryptocurrency-based reward may be generated in response to identifying the satisfaction of the first achievement threshold. The cryptocurrency-based reward may be an example of a cryptocurrency token, a non-fungible token, a smart-contract enabled token, or a combination thereof.

At 540, a second threshold may be identified. For example, the application 505 may identify a satisfaction of a second achievement threshold corresponding to a second alternate icon of the alternate icons. In some cases, the second achievement threshold may be identified in response to processing the data received at the application 505 from at least the wearable device or other sources. In some examples, the application 505 may identify that the second threshold is satisfied, and the user has achieved another accomplishment (e.g., in addition to the first achievement) within the application 505 in response to receiving the physiological data.

The application 505 may use physiological data measured by the wearable device to identify that the second threshold is met to unlock a second alternate application icon. For example, the application 505 may identify that the user ran five miles each day for the past week, and the alternate icon corresponding to an activity-based achievement may be unlocked. In such cases, the second threshold may be an example of five miles ran each day for the past week.

In other examples, the application 505 may identify that the second threshold is satisfied, and the user has achieved another accomplishment (e.g., in addition to the first achievement) within the application 505 in response to receiving data from other sources such as a a social media account. The application 505 may use the data received to identify that the second threshold is met to unlock a second alternate application icon. For example, the application 505 may identify that the user met their goal of sharing one post per day on their social media account, and the alternate icon corresponding to the social media-based achievement may be unlocked. In such cases, the second threshold may be an example of sharing at least one social media post a day for the past month.

At 545, the second alternate icon may be selected. For example, the application 505 may receive an indication of selection of the second alternate icon after identifying the satisfaction of the first achievement threshold and the second achievement threshold. In some examples, the application 505 may output, to the user interface of the application 505, a request to select the first alternate icon or the second alternate icon in response to identifying the satisfaction of the second achievement threshold. The application 505 may select the second alternate icon in response to receiving an indication of selection of the second alternate icon. In such cases, the application 505 may select an alternate application icon from a list of alternate application icons that have been previously unlocked.

In some cases, in response to outputting the request to select the first alternate icon or the second alternate icon, the application 505 may receive an indication of selection of the first alternate icon. In such cases, the application 505 may output the visual display instruction to display the first alternate icon instead of the default icon and instead of the second alternate icon that has been unlocked. The visual display instruction may include an instruction to maintain displaying the first alternate icon despite the second alternate icon becoming available for use.

At 550, the second visual display instruction may be outputted. For example, the application 505 may generate the second visual display instruction and output the second visual display instruction to the operating system 510 of the user device. The second visual display instruction may include an instruction to display a second alternate icon of the alternate icons on the user interface of the user device instead of the first alternate icon. In some cases, the second visual display instruction may include an instruction to display a second alternate icon of the alternate icons on the user interface of the user device instead of the default icon. The second visual display instruction may be outputted in response to outputting the request.

The second alternate icon is visually representative of a type of achievement (e.g., a sleep achievement, an activity achievement, a recovery achievement, and the like) corresponding to the second achievement threshold. For example, the visual display instruction may include an instruction for switching the first alternate icon to the second alternate icon. In such cases, the first alternate icon may be changed and/or updated to the second unlocked application icon. For example, the second alternate application icon may be visually representative of the activity-based achievement corresponding to the user running five miles each day for the past week or the social media-based achievement corresponding to the user sharing a single post every day for the past month.

The system (e.g., including at least the application 505 and the operating system 510) may optimize the user experience such that the home screen icons may indicate that the user has achieved an accomplishment within the application 505. In such cases, the user may select which accomplishment they wish to display external the application 505, thereby making the application icon more engaging and personal to the user.

Figure 6:
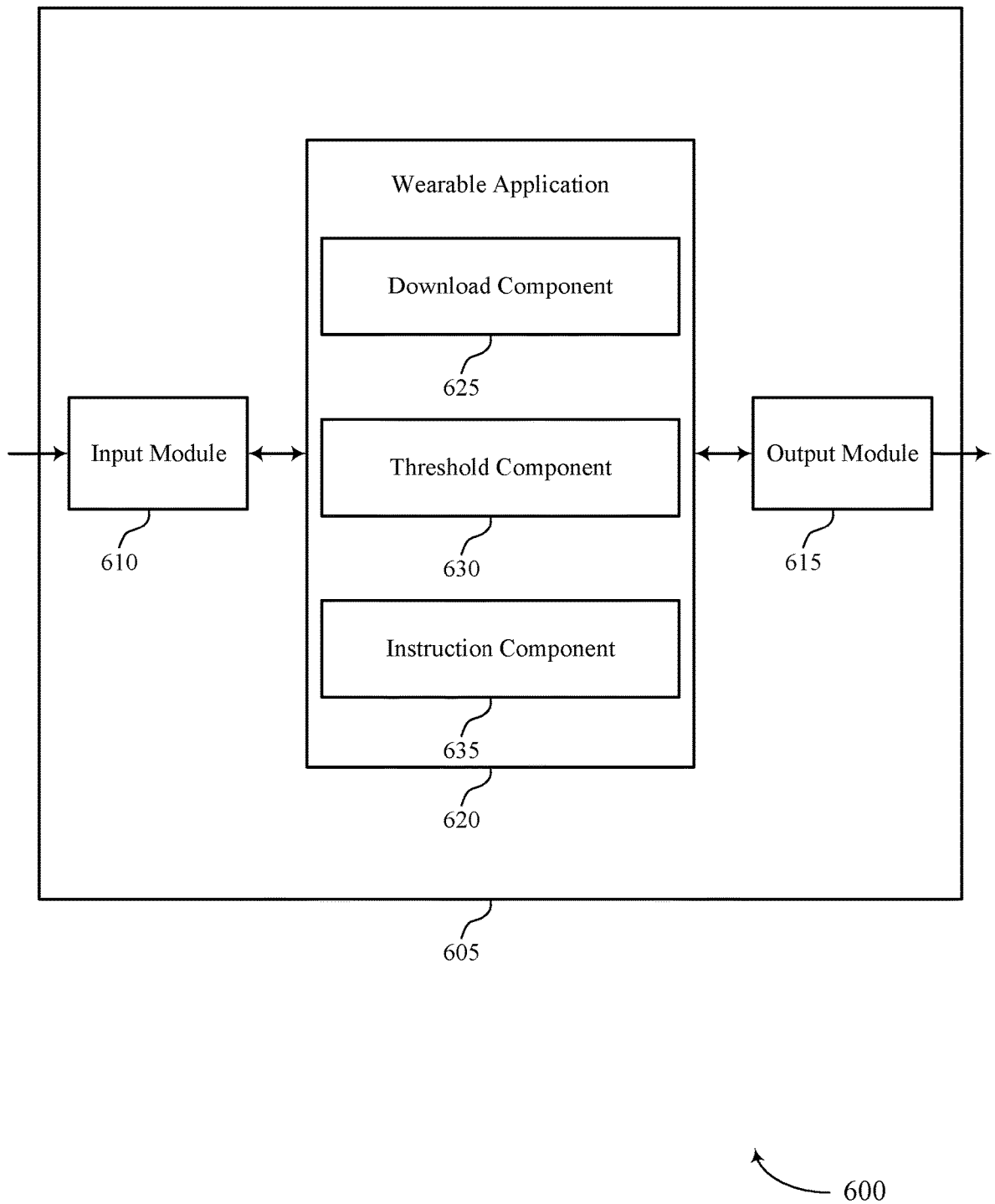
FIG. 6 shows a block diagram of an apparatus that supports dynamic application icons in accordance with aspects of the present disclosure.

FIG. 6 shows a block diagram 600 of a device 605 that supports dynamic application icons in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a download component 625, a threshold component 630, an instruction component 635, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The download component 625 may be configured as or otherwise support a means for receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds. The threshold component 630 may be configured as or otherwise support a means for identifying a satisfaction of a first achievement threshold of the one or more achievement thresholds corresponding to a first alternate icon of the one or more alternate icons based at least in part on processing data received at the application. The instruction component 635 may be configured as or otherwise support a means for outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

Figure 7:
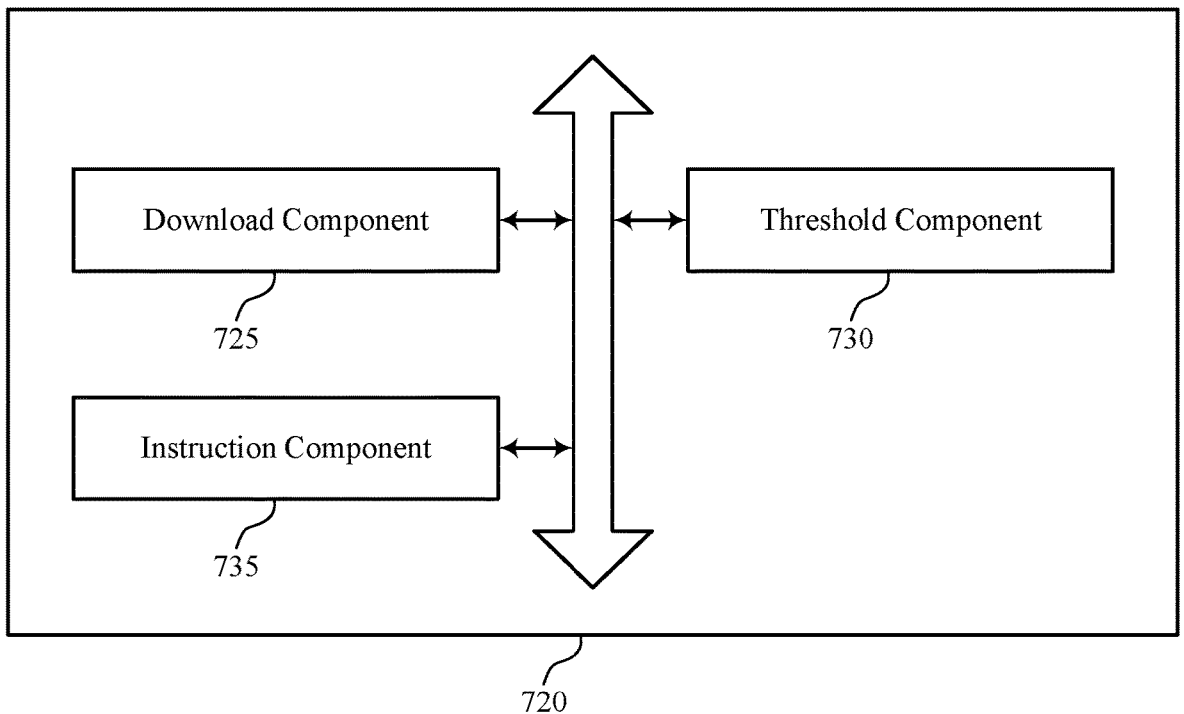
FIG. 7 shows a block diagram of a wearable application that supports dynamic application icons in accordance with aspects of the present disclosure.

FIG. 7 shows a block diagram 700 of a wearable application 720 that supports dynamic application icons in accordance with aspects of the present disclosure. The wearable application 720 may be an example of aspects of a wearable application or a wearable application 620, or both, as described herein. The wearable application 720, or various components thereof, may be an example of means for performing various aspects of dynamic application icons as described herein. For example, the wearable application 720 may include a download component 725, a threshold component 730, an instruction component 735, or any combination thereof. Each of these components may communicate, directly or indirectly, with one another (e.g., via one or more buses).

The download component 725 may be configured as or otherwise support a means for receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds. The threshold component 730 may be configured as or otherwise support a means for identifying a satisfaction of a first achievement threshold of the one or more achievement thresholds corresponding to a first alternate icon of the one or more alternate icons based at least in part on processing data received at the application. The instruction component 735 may be configured as or otherwise support a means for outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

In some examples, the threshold component 730 may be configured as or otherwise support a means for receiving, at the application, physiological data measured from a user by a wearable device, wherein identifying the satisfaction of the first achievement threshold is based at least in part on receiving the physiological data.

In some examples, the physiological data comprises sleep data, recovery data, activity data, heart rate data, breathing rate data, blood pressure data, blood glucose data, or a combination thereof.

In some examples, the visual display instruction comprises an instruction for switching the default icon to the first alternate icon of the one or more alternate icons.

In some examples, the threshold component 730 may be configured as or otherwise support a means for identifying a satisfaction of a second achievement threshold of the one or more achievement thresholds corresponding to a second alternate icon of the one or more alternate icons based at least in part on processing data received at the application from at least a wearable device. In some examples, the instruction component 735 may be configured as or otherwise support a means for outputting, to the user interface of the application; a request to select the first alternate icon or the second alternate icon based at least in part on identifying the satisfaction of the second achievement threshold. In some examples, the instruction component 735 may be configured as or otherwise support a means for outputting, to the operating system of the user device, a second visual display instruction to display the second alternate icon of the one or more alternate icons on the user interface of the user device instead of the first alternate icon based at least in part on outputting the request, wherein the second alternate icon is visually representative of a type of achievement corresponding to the second achievement threshold.

In some examples, the instruction component 735 may be configured as or otherwise support a means for generating a cryptocurrency-based reward for the user based at least in part on identifying the satisfaction of the first achievement threshold.

In some examples, the cryptocurrency-based reward comprises a cryptocurrency token, a non-fungible token, a smart-contract enabled token, or a combination thereof.

In some examples, the download component 725 may be configured as or otherwise support a means for identifying a hardware attribute of a wearable device based at least in part on receiving the application software package, wherein the one or more alternate icons are based at least in part on the type of hardware.

In some examples, the one or more achievement thresholds comprise a value corresponding to an activity-based achievement, a sleep-based achievement, a readiness-based achievement, a recovery-based achievement, or a combination thereof.

In some examples, the type of achievement comprises an activity-based achievement, a sleep-based achievement, a readiness-based achievement, a recovery-based achievement, or a combination thereof.

In some examples, the wearable device comprises a finger-worn device, a wrist-worn device, a patch, a head-worn device, a chest-worn device, or a combination thereof.

Figure 8:
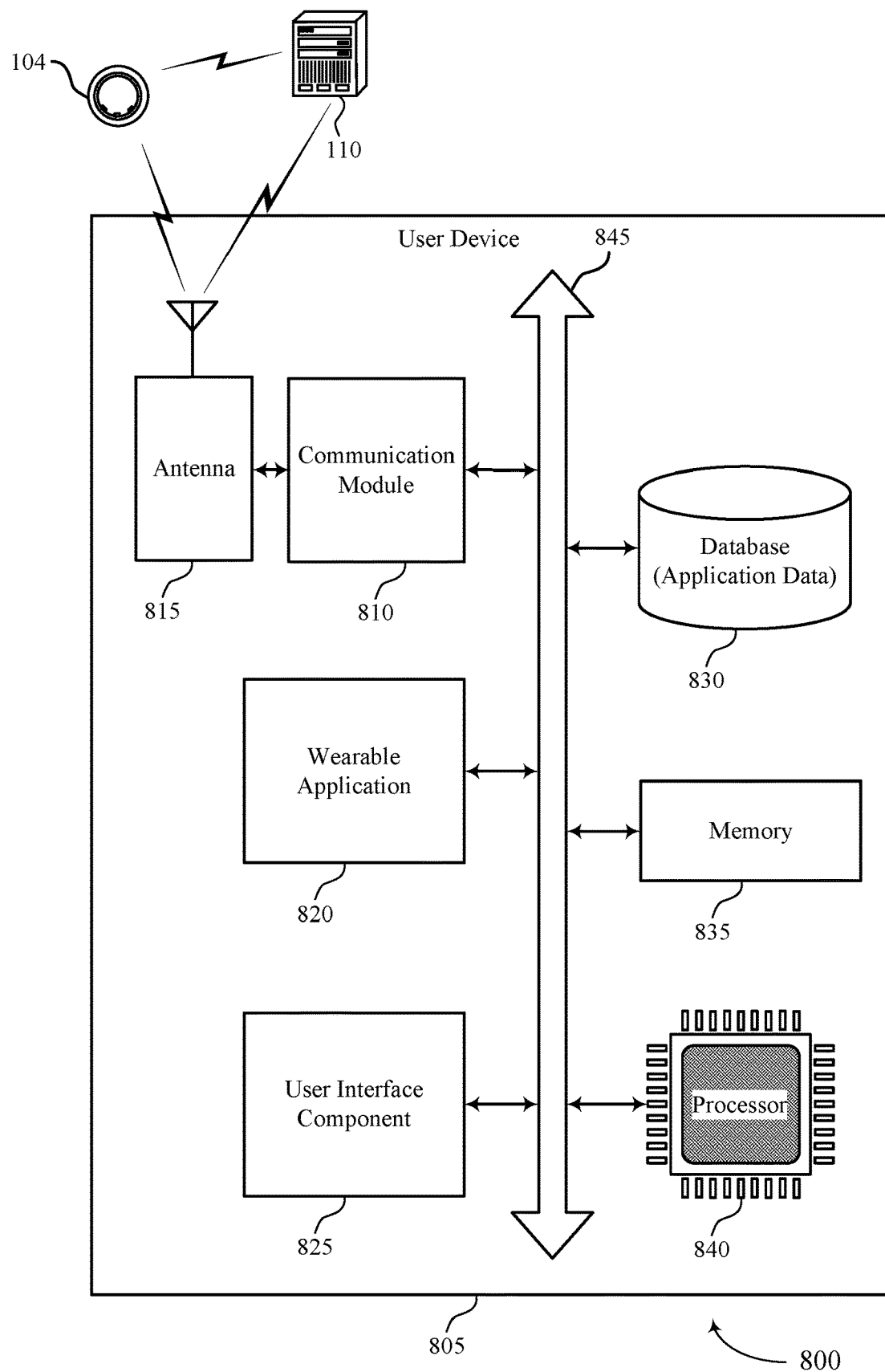
FIG. 8 shows a diagram of a system including a device that supports dynamic application icons in accordance with aspects of the present disclosure.

FIG. 8 shows a diagram of a system 800 including a device 805 that supports dynamic application icons in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-*b* of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, that may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS that may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

For example, the wearable application 820 may be configured as or otherwise support a means for receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds. The wearable application 820 may be configured as or otherwise support a means for identifying a satisfaction of a first achievement threshold of the one or more achievement thresholds corresponding to a first alternate icon of the one or more alternate icons based at least in part on processing data received at the application. The wearable application 820 may be configured as or otherwise support a means for outputting, to the operating system of the user device, a visual display instruction to displaying the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

By including or configuring the wearable application 820 in accordance with examples as described herein, the device 805 may support techniques for improved communication reliability, improved user experience, more efficient utilization of communication resources, improved coordination between devices, improved utilization of processing capability, and the like.

The wearable application 820 may include an application (e.g., "app"), program, software, or other component that is configured to facilitate communications with a ring 104, server 110, other user devices 106, and the like. For example, the wearable application 820 may include an application executable on a user device 106 that is configured to receive data (e.g., physiological data) from a ring 104, perform processing operations on the received data, transmit and receive data with the servers 110, and cause presentation of data to a user 102.

Figure 9:
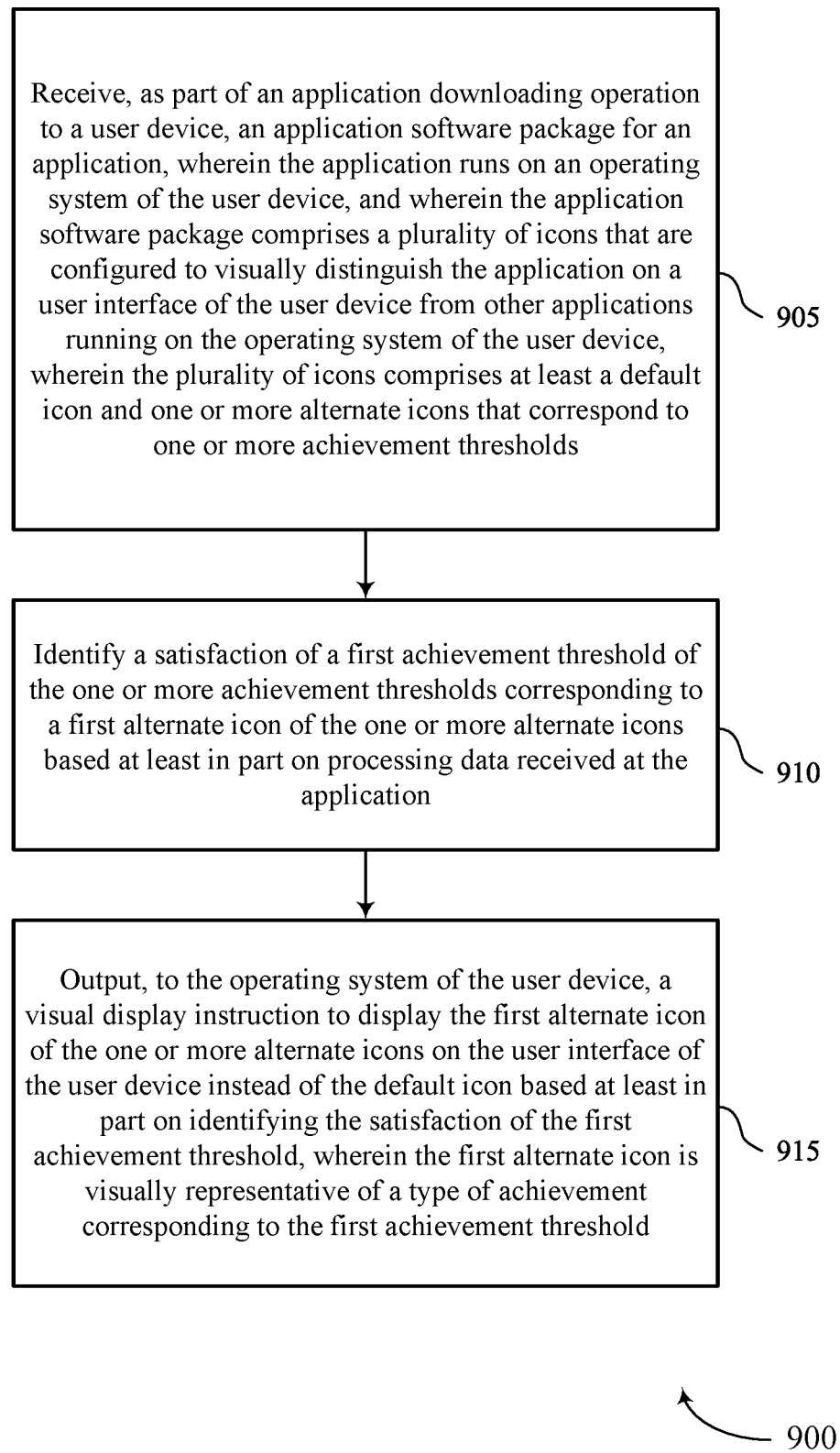
FIG. 9 shows a flowchart illustrating methods that support dynamic application icons in accordance with aspects of the present disclosure.

FIG. 9 shows a flowchart illustrating a method 900 that supports dynamic application icons in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the wireless user device to perform the described functions. Additionally, or alternatively, the wireless user device may perform aspects of the described functions using special-purpose hardware.

At 905, the method may include receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds. The operations of 905 may be performed in accordance with examples as disclosed herein. In some examples, aspects of the operations of 905 may be performed by a download component 725 as described with reference to FIG. 7.

At 910, the method may include identifying a satisfaction of a first achievement threshold of the one or more achievement thresholds corresponding to a first alternate icon of the one or more alternate icons based at least in part on processing data received at the application. The operations of 910 may be performed in accordance with examples as disclosed herein. In some examples, aspects of the operations of 910 may be performed by a threshold component 730 as described with reference to FIG. 7.

At 915, the method may include outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold. The operations of 915 may be performed in accordance with examples as disclosed herein. In some examples, aspects of the operations of 915 may be performed by an instruction component 735 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method is described. The method may include receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds, identifying a satisfaction of a first achievement threshold of the one or more achievement thresholds corresponding to a first alternate icon of the one or more alternate icons based at least in part on processing data received at the application, and outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

An apparatus is described. The apparatus may include a processor, memory coupled with the processor, and instructions stored in the memory. The instructions may be executable by the processor to cause the apparatus to receive, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds, identify a satisfaction of a first achievement threshold of the one or more achievement thresholds corresponding to a first alternate icon of the one or more alternate icons based at least in part on processing data received at the application, and outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

Another apparatus is described. The apparatus may include means for receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds, means for identifying a satisfaction of a first achievement threshold of the one or more achievement thresholds corresponding to a first alternate icon of the one or more alternate icons based at least in part on processing data received at the application, and means for outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

A non-transitory computer-readable medium storing code is described. The code may include instructions executable by a processor to receive, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds, identify a satisfaction of a first achievement threshold of the one or more achievement thresholds corresponding to a first alternate icon of the one or more alternate icons based at least in part on processing data received at the application, and outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

Some examples of the method, apparatuses, and non-transitory computer-readable medium described herein may further include operations, features, means, or instructions for receiving, at the application, physiological data measured from a user by a wearable device, wherein identifying the satisfaction of the first achievement threshold may be based at least in part on receiving the physiological data.

In some examples of the method, apparatuses, and non-transitory computer-readable medium described herein, the physiological data comprises sleep data, recovery data, activity data, heart rate data, breathing rate data, blood pressure data, blood glucose data, or a combination thereof.

In some examples of the method, apparatuses, and non-transitory computer-readable medium described herein, the visual display instruction comprises an instruction for switching the default icon to the first alternate icon of the one or more alternate icons.

Some examples of the method, apparatuses, and non-transitory computer-readable medium described herein may further include operations, features, means, or instructions for identifying a satisfaction of a second achievement threshold of the one or more achievement thresholds corresponding to a second alternate icon of the one or more alternate icons based at least in part on processing data received at the application from at least a wearable device, outputting, to the user interface of the application; a request to select the first alternate icon or the second alternate icon based at least in part on identifying the satisfaction of the second achievement threshold, and outputting, to the operating system of the user device, a second visual display instruction to display the second alternate icon of the one or more alternate icons on the user interface of the user device instead of the first alternate icon based at least in part on outputting the request, wherein the second alternate icon may be visually representative of a type of achievement corresponding to the second achievement threshold.

Some examples of the method, apparatuses, and non-transitory computer-readable medium described herein may further include operations, features, means, or instructions for generating a cryptocurrency-based reward for the user based at least in part on identifying the satisfaction of the first achievement threshold.

In some examples of the method, apparatuses, and non-transitory computer-readable medium described herein, the cryptocurrency-based award comprises a cryptocurrency token, a non-fungible token, a smart-contract enabled token, or a combination thereof.

Some examples of the method, apparatuses, and non-transitory computer-readable medium described herein may further include operations, features, means, or instructions for identifying a hardware attribute of a wearable device based at least in part on receiving the application software package, wherein the one or more alternate icons may be based at least in part on the type of hardware.

In some examples of the method, apparatuses, and non-transitory computer-readable medium described herein, the one or more achievement thresholds comprise a value corresponding to an activity-based achievement, a sleep-based achievement, a readiness-based achievement, a recovery-based achievement, or a combination thereof.

In some examples of the method, apparatuses, and non-transitory computer-readable medium described herein, the type of achievement comprises an activity-based achievement, a sleep-based achievement, a readiness-based achievement, a recovery-based achievement, or a combination thereof.

In some examples of the method, apparatuses, and non-transitory computer-readable medium described herein, the wearable device comprises a finger-worn device, a wrist-worn device, a patch, a head-worn device, a chest-worn device, or a combination thereof.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method, comprising:
   receiving, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds;
   identifying a satisfaction of a first achievement threshold of the one or more achievement thresholds corresponding to a first alternate icon of the one or more alternate icons based at least in part on processing data received at the application; and
   outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

2. The method of claim 1, further comprising:
   receiving, at the application, physiological data measured from a user by a wearable device, wherein identifying the satisfaction of the first achievement threshold is based at least in part on receiving the physiological data.

3. The method of claim 2, wherein the physiological data comprises sleep data, recovery data, activity data, heart rate data, breathing rate data, blood pressure data, blood glucose data, or a combination thereof.

4. The method of claim 2, wherein the wearable device comprises a finger-worn device, a wrist-worn device, a patch, a head-worn device, a chest-worn device, or a combination thereof.

5. The method of claim 1, wherein the visual display instruction comprises an instruction for switching the default icon to the first alternate icon of the one or more alternate icons.

6. The method of claim 1, further comprising:
   identifying a satisfaction of a second achievement threshold of the one or more achievement thresholds corresponding to a second alternate icon of the one or more alternate icons based at least in part on processing data received at the application from at least a wearable device;
   outputting, to the user interface of the application; a request to select the first alternate icon or the second alternate icon based at least in part on identifying the satisfaction of the second achievement threshold; and
   outputting, to the operating system of the user device, a second visual display instruction to display the second alternate icon of the one or more alternate icons on the user interface of the user device instead of the first alternate icon based at least in part on outputting the request, wherein the second alternate icon is visually representative of a type of achievement corresponding to the second achievement threshold.

7. The method of claim 1, further comprising:
   identifying a hardware attribute of a wearable device based at least in part on receiving the application software package, wherein the one or more alternate icons are based at least in part on the type of hardware.

8. The method of claim 1, wherein the one or more achievement thresholds comprise a value corresponding to an activity-based achievement, a sleep-based achievement, a readiness-based achievement, a recovery-based achievement, or a combination thereof.

9. The method of claim 1, wherein the type of achievement comprises an activity-based achievement, a sleep-based achievement, a readiness-based achievement, a recovery-based achievement, or a combination thereof.

10. The method of claim 1, further comprising:
    generating a cryptocurrency-based reward for the user based at least in part on identifying the satisfaction of the first achievement threshold.

11. The method of claim 10, wherein the cryptocurrency-based reward comprises a cryptocurrency token, a non-fungible token, a smart-contract enabled token, or a combination thereof.

12. An apparatus, comprising:
    a processor;
    memory coupled with the processor; and
    instructions stored in the memory and executable by the processor to cause the apparatus to:
        receive, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds;
        identify a satisfaction of a first achievement threshold of the one or more achievement thresholds corresponding to a first alternate icon of the one or more alternate icons based at least in part on processing data received at the application; and
        outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

13. The apparatus of claim 12, wherein the instructions are further executable by the processor to cause the apparatus to:
receive, at the application, physiological data measured from a user by awearable device, wherein identifying the satisfaction of the first achievement threshold is based at least in part on receiving the physiological data.

14. The apparatus of claim 13, wherein the physiological data comprises sleep data, recovery data, activity data, heart rate data, breathing rate data, blood pressure data, blood glucose data, or a combination thereof.

15. The apparatus of claim 12, wherein the visual display instruction comprises an instruction for switching the default icon to the first alternate icon of the one or more alternate icons.

16. The apparatus of claim 12, wherein the instructions are further executable by the processor to cause the apparatus to:
identify a satisfaction of a second achievement threshold of the one or more achievement thresholds corresponding to a second alternate icon of the one or more alternate icons based at least in part on processing data received at the application from at least the wearable device;
outputting, to the user interface of the application; a request to select the first alternate icon or the second alternate icon based at least in part on identifying the satisfaction of the second achievement threshold; and
outputting, to the operating system of the user device, a second visual display instruction to display the second alternate icon of the one or more alternate icons on the user interface of the user device instead of the first alternate icon based at least in part on outputting the request, wherein the second alternate icon is visually representative of a type of achievement corresponding to the second achievement threshold.

17. The apparatus of claim 12, wherein the instructions are further executable by the processor to cause the apparatus to:
identify a hardware attribute of a wearable device based at least in part on receiving the application software package, wherein the one or more alternate icons are based at least in part on the type of hardware.

18. The apparatus of claim 12, wherein the one or more achievement thresholds comprise a value corresponding to an activity-based achievement, a sleep-based achievement, a readiness-based achievement, a recovery-based achievement, or a combination thereof.

19. A non-transitory computer-readable medium storing code, the code comprising instructions executable by a processor to:
receive, as part of an application downloading operation to a user device, an application software package for an application, wherein the application runs on an operating system of the user device, and wherein the application software package comprises a plurality of icons that are configured to visually distinguish the application on a user interface of the user device from other applications running on the operating system of the user device, wherein the plurality of icons comprises at least a default icon and one or more alternate icons that correspond to one or more achievement thresholds;
identify a satisfaction of a first achievement threshold of the one or more achievement thresholds corresponding to a first alternate icon of the one or more alternate icons based at least in part on processing data received at the application; and
outputting, to the operating system of the user device, a visual display instruction to display the first alternate icon of the one or more alternate icons on the user interface of the user device instead of the default icon based at least in part on identifying the satisfaction of the first achievement threshold, wherein the first alternate icon is visually representative of a type of achievement corresponding to the first achievement threshold.

20. The non-transitory computer-readable medium of claim 19, wherein the instructions are further executable by the processor to:
receive, at the application, physiological data measured from a user by a wearable device, wherein identifying the satisfaction of the first achievement threshold is based at least in part on receiving the physiological data.

* * * * *